United States Patent
Anglada Cortes et al.

(10) Patent No.: US 11,393,567 B1
(45) Date of Patent: Jul. 19, 2022

(54) SYSTEMS AND METHODS FOR IMPROVING COMPLIANCE WITH A CUSTOMIZED MEDICAL CARE PLAN

(71) Applicant: HOY HEALTH LLC, Greer, SC (US)

(72) Inventors: Mario R. Anglada Cortes, Greenville, SC (US); José Miguel Febus Rodriguez, San Juan, PR (US)

(73) Assignee: Hoy Health LLC, Greer, SC (US)

( * ) Notice: Subject to any disclaimer, the term of this patent is extended or adjusted under 35 U.S.C. 154(b) by 0 days.

(21) Appl. No.: 17/488,599

(22) Filed: Sep. 29, 2021

(51) Int. Cl.
| | |
|---|---|
| G16H 20/00 | (2018.01) |
| G16H 10/60 | (2018.01) |
| A61B 5/00 | (2006.01) |
| G16H 40/67 | (2018.01) |
| G16H 40/20 | (2018.01) |
| G16H 50/20 | (2018.01) |

(52) U.S. Cl.
CPC ........... *G16H 20/00* (2018.01); *A61B 5/4833* (2013.01); *G16H 10/60* (2018.01); *G16H 40/20* (2018.01); *G16H 40/67* (2018.01); *G16H 50/20* (2018.01)

(58) Field of Classification Search
CPC ........ G16H 50/30; G16H 20/10; G16H 20/60; G16H 20/30; G16H 80/00; G16H 20/00; G16H 40/63; G16H 40/67; G06F 21/604
See application file for complete search history.

(56) References Cited

U.S. PATENT DOCUMENTS

| | | | | |
|---|---|---|---|---|
| 2008/0109747 A1* | 5/2008 | Cao | ........................ | G06F 16/958 715/780 |
| 2011/0313258 A1* | 12/2011 | Chopra | ................... | G16H 40/67 600/300 |
| 2017/0039324 A1* | 2/2017 | Francois | ................ | G16H 10/60 |
| 2017/0235909 A1* | 8/2017 | Lozano | ............. | G09B 19/0092 705/3 |
| 2021/0045682 A1* | 2/2021 | Poon | .................... | A61B 5/6802 |

OTHER PUBLICATIONS

V. G. Koutkias, I. Chouvarda and N. Maglaveras, "A multiagent system enhancing home-care health services for chronic disease management," in IEEE Transactions on Information Technology in Biomedicine, vol. 9, No. 4, pp. 528-537, Dec. 2005, doi: 10.1109/TITB.2005.847511. (Year: 2005).*

* cited by examiner

*Primary Examiner* — Joseph D Burgess
(74) *Attorney, Agent, or Firm* — Polsinelli PC

(57) ABSTRACT

The disclosed technology relates to a platform for providing improved compliance with a customized medical care plan. A customized medical care plan is generated based on a health condition of a user. A first measurement is solicited at a first predetermined time period. The first measurement is received from a measurement device within the first predetermined time period. A compliance score is generated based on receipt of the first measurement within the first predetermined time period. An intervention can be initiated based on the generated compliance score and the first measurement.

20 Claims, 8 Drawing Sheets

SYSTEMS AND METHODS FOR IMPROVING COMPLIANCE WITH A CUSTOMIZED MEDICAL CARE PLAN

TECHNICAL FIELD

The present disclosure relates generally to systems and methods for providing healthcare, and more particularly to a healthcare system and method that provides improved compliance to a customized medical care plan.

BACKGROUND

Treatment of a medical condition may involve tracking of measurements of the patient's health and/or taking medications over a period of time. The timing and consistency of taking the measurements and/or medications provides the data for a medical professional to know if the treatment is working and/or if the medical condition is improving. As a result, a patient may have trouble complying with treatment plans and/or adhering to medication prescriptions, which may ultimately lead to a worsening of the medical condition for which treatment was originally sought. Compliance of the patient with the medical care plan is critical to the success of the medical care plan.

SUMMARY

According to various aspects of the subject technology, a healthcare system and method that provides improved accountability for adherence to a health plan via an integrated delivery platform is provided. According to aspects of the subject technology, a method for improving compliance with a customized medical care plan is disclosed. The method includes providing, via a user device, a customized medical care plan based on a health condition of a user. The customized medical care plan may include solicitations for a plurality of measurements, with each measurement to be captured within a corresponding predetermined time period. A first measurement is solicited at a first predetermined time period according to the customized medical care plan. The first measurement is received within the first predetermined time period. A compliance score is generated based on receipt of the first measurement within the first predetermined time period. An intervention is initiated based on the generated compliance score and the first measurement.

Another aspect of the present disclosure relates to a medical care compliance system. The system may include one or more processors and a non-transitory computer-readable medium storing instructions that, when executed by the processors, cause the processors to perform operations comprising: generating a customized medical care plan based on a health condition of a user, the customized medical care plan including solicitations for a plurality of measurements, each measurement to be captured within a corresponding predetermined time period; soliciting a first measurement of the plurality of measurements within a first predetermined time period according to the customized medical care plan; generating a compliance score based on receipt of the first measurement within the first predetermined time period; and initiating an intervention based on the generated compliance score and the first measurement.

Yet another aspect of the present disclosure relates to a non-transient computer-readable storage medium having instructions embodied thereon, the instructions being executable by one or more processors to perform operations comprising: generating a customized medical care plan based on a health condition of a user, the customized medical care plan including solicitations for a plurality of measurements, each measurement to be captured within a corresponding predetermined time period; soliciting a first measurement of the plurality of measurements within a first predetermined time period according to the customized medical care plan; generating a compliance score based on receipt of the first measurement within the first predetermined time period; and initiating an intervention based on the generated compliance score and the first measurement.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The embodiments herein may be better understood by referring to the following description in conjunction with the accompanying drawings in which like reference numerals indicate identical or functionally similar elements. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
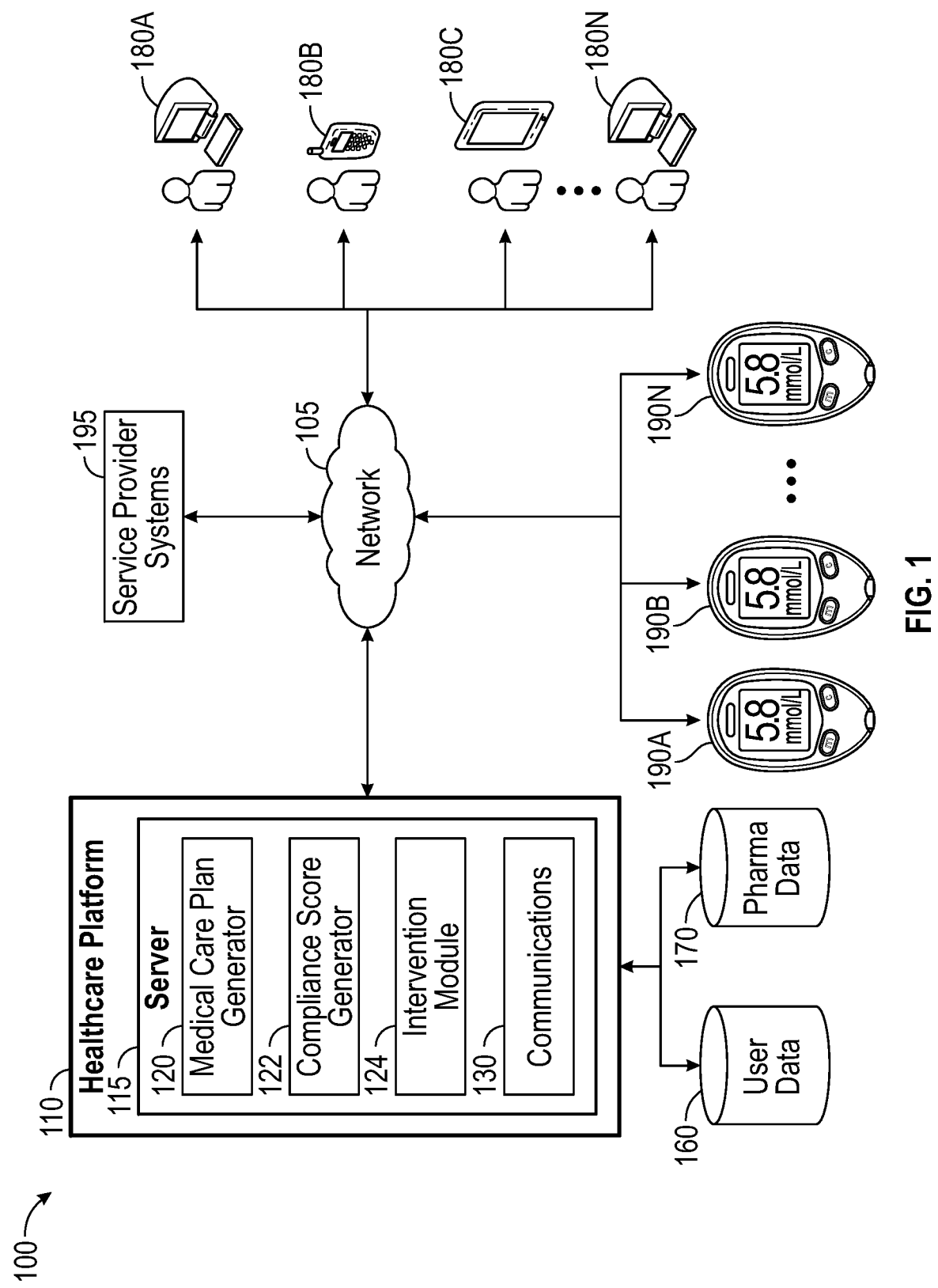
FIG. 1 illustrates a conceptual block diagram illustrating an example network environment utilizing a healthcare platform, in accordance with various aspects of the subject technology.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

The disclosed subject matter describes systems and methods for providing healthcare using a healthcare platform. A customized medical care plan can be generated and provided to a user device. The customized medical care plan can include solicitations for a plurality of measurements, each measurement to be captured within a corresponding predetermined time period. Based on receipt and/or non-receipt of the measurements within the corresponding predetermined time periods, a compliance score can be generated. Based on the compliance score and/or one or more measurements, an intervention can be initiated to help the user comply with the medical care plan. To also ensure accuracy of the measurements, upon receipt of a measurement, prior solicitations for the plurality of measurements is disabled.

The disclosed technology addresses the need in the art for more effective patient care technologies by utilizing a platform to collect and aggregate data from disparate sources to generate a customized medical care plan to treat a medical condition, and to utilize new data collected from a user device associated with the user to improve adherence and compliance to the medical care plan. The platform is configured to transmit the medical care plan to the user device associated with the user and in response, the user device is configured to execute instructions associated with the recommendation to remind, prompt, or encourage the user to follow the medical care plan (e.g., take medication, engage in physical activity, take a test, etc.) and/or gather data regarding a health characteristic of the user (e.g., movement data, blood test data, user weight data, etc.). A compliance score can be generated based on the user's activity following the medical care plan, and an intervention can be initiated based on the compliance score; thereby improving medical care plan adherence and management of medical conditions.

These and other embodiments address various technical problems in the computing field as well. For example, the various approaches taken address the shortcomings in the various application program interfaces (APIs) and/or proprietary data structures provided by disparate consumer products that collect user data, such as wearables, pedometers, blood pressure reading devices, blood test sample devices, scales, heartrate monitors, and other devices that may be configured to collect and present certain data to the user, but do not make such data available to other devices or platforms. Structural limitations of such data further prevent robust querying of data sets. Additionally, the various approaches further reduce the bandwidth and processing time required to perform various functions.

FIG. 1 illustrates a conceptual block diagram illustrating an example network environment 100 utilizing a healthcare platform 110, in accordance with various aspects of the subject technology. The integrated delivery platform 110 may comprise a one or more servers 115 connected via a network 105. The one or more servers 115 may be configured to communicate with one or more user devices 180A-N according to a client/server architecture and/or other architectures. Users may access the platform 110 via the user devices 180A-N. The servers 115 may be configured by machine-readable instructions. Machine-readable instructions may include one or more instruction modules. The instruction modules may include computer program modules. The instruction modules may include one or more of a medical care plan generator 120, a compliance score generator 122, an intervention module 124, a communications module 130, and/or other instruction modules.

The one or more servers 115 may be any system or device having a processor, a memory, and communications capability for receiving data from and providing instructions to the user devices 180A-N. In some example aspects, the one or more servers 115 can be a single computing device such as a single computer server. In other embodiments, the one or more servers 115 can represent more than one computing device working together to perform the actions of a server computer (e.g., cloud computing).

The network 105 can include, for example, any one or more of a cellular network, a satellite network, a personal area network (PAN), a local area network (LAN), a wide area network (WAN), a broadband network (BBN), the Internet, Bluetooth, radio frequency identification (RFID), and/or the like. Further, the network 105 can include, but is not limited to, any one or more of the following network topologies, including a bus network, a star network, a ring network, a mesh network, a star-bus network, tree or hierarchical network, and the like.

The one or more servers 115 may be configured to access a database 160 that is configured to store data associated with a user. User data may include, for example, data relating to prior medication purchases, medical records from healthcare organizations, medical condition, biometric data, genetic data, health literacy data, telehealth consultation data, wearable device data, medication adherence data, family composition data, email, contact information, user device information (e.g., MAC address), address, chat data, supplement and vitamin use, retail purchase data, condition predictive algorithm data, health condition status, and/or chat bot data. Each user may be keyed to a user ID and the user database 160 may include information for user devices 180A-N associated to a particular user.

In some aspects, user data may be stored in accordance with regulations, such as HIPAA. As such, data stored in user database 160 may be segmented such that data that may identify a user may be removed from medical data. In such an example, minimal user data (e.g., (user ID, first and last name, email, date of birth, and/or address) may be stored in a HIPAA compliant data store, and data relating to prior medication purchases, medical records from healthcare organizations, medical condition, biometric data, genetic data, health literacy data, telehealth consultation data, wearable device data, medication adherence data, family composition data, supplement and vitamin use, retail purchase data, condition predictive algorithm data, health condition status, and/or chat bot data may be stored in an anonymous data store. The data in the anonymous data store may be keyed by the user ID which represents a unique alphanumeric or numeric code (e.g., 339fj3-33d4-fkfkf-33e3) that yields no identifying information on its own.

Data in the user database 160 may be populated in batch processes by querying one or more third-party data providers such as service provider systems 195, by storing information provided by the user device 180A-N, and/or by storing information provided by one or more measurement devices 190A-N. According to some embodiments, data is available to the platform 110 and may be replicated and stored locally in order to address the technical problem caused by disparate systems that do not provide sophisticated APIs and backend functionality that enable fast and efficient querying. In other aspects, storing user data in database 160 allows for more complex queries, which allows for more efficient and powerful segmentation and targeting of the users that will receive a customized medical care plan. For example, depending on the compliance with the user's medical care plan, the healthcare platform 110 may adjust the medical care plan and/or transmit an alert to the service provide systems 195 to initiate an intervention.

The medical care plan generator 120 may be configured to analyze data stored in the user database 160 and/or data stored in pharmaceutical database 170 to generate a customized medical care plan. In one aspect, the medical care plan generator 120 may generate a digital record of the user that may be used to effectively engage users and address their unique medical needs. Data stored in the database 160, 170 and/or analyzed by the medical care plan generator 120 may be stored and transmitted in a secure block chain. The medical care plan may, for example, include medication, measurements, and/or recommend devices 190A-N that are intended to treat a medical condition of the user.

The compliance score generator 122 may generate a compliance score. The compliance score can indicate and be based on how well a patient is following the medical care plan. In some examples, the compliance score can be generated based on receipt or non-receipt of the remaining measurements of the plurality of measurements that are captured within the corresponding predetermined time periods. For example, the compliance score can be generated based on a percentage of receipt versus non-receipt of measurements within the predetermined time periods. In some examples, different measurements may be weighted based on importance.

The intervention module 124 may issue an intervention to the user to improve compliance with the medical care plan. The intervention module 124 may determine whether to initiate an intervention based on the compliance score generated by the compliance score generator 122. In some examples, the intervention module 124 may determine whether to initiate an intervention based on the measurements received or not received from the measurement devices 190A-N based on the medical care plan. For example, the intervention module 124 may communicate with the service provider systems 195 to initiate an intervention where the service provider can reach out to the patient. In some examples, the intervention module 124 may initiate an intervention by providing notifications or alerts to the user to encourage the user to better comply with the medical care plan.

The communications module 130 may be configured to communicate with a user via the user device 180A-N. The user device 180A-N may be capable of running an application and communicating with the platform 110, to provide the user with the customized medical care plan, instructions for how to capture a medical reading/measurement using a medical device 190A-N, solicitations for taking a medical reading/measurement, and/or an alert or intervention to aid in the treatment of a medical condition. The user device 180A-N may be a mobile phone, PDA, portable media player, tablet, laptop, or other appropriate computing device, and may utilize a touch sensitive user interface, such as a touch-sensitive screen, to receive user input. The touch screen of the user device 180A-N may be built into the device itself, or can be electronically connected to the device (e.g., as a measurement device 190A-N). The user input may comprise gestures or touch. In some example aspects, the user device 180A-N may be any machine with appropriate hardware/software to launch and run one or more applications or software.

One or more of the applications may include application data comprising a graphical user interface. The application may thus, be configured to receive user input using the graphical user interface and the touch-sensitive screen. The application's graphical user interface may include touch elements that are displayed to the user and configured to trigger an application function based on user input.

Measurement devices 190A-N may include peripherals, such as glucometers, oxygenation monitor, spirometer, heart monitors, blood pressure monitors, scales, or other devices that may be used to collect information or data about a user and transmit the collected information or data to the user device 180A-N and/or platform 110 for storage in the database 160 and analyzing by the medical care plan generator 120, compliance score generator 122, and/or intervention module 124.

In some examples, the measurement devices 190A-N can be communicatively coupled with the user device(s) 180A-N, for example via Bluetooth. In some examples, the measurement devices 190A-N can automatically, without user interference or manipulation, couple with the user device 180A-N upon a signal from the user device 180A-N to solicit a measurement. In some examples, the measurement device 190A-N can send the measurement directly to the user device 180A-N without relying on a user to input the measurement. When the measurement device 190A-N automatically couples with and/or sends a measurement to the user device 180A-N, the user is not able to manipulate, cheat, or fake their compliance or measurements. Accordingly, the determination of the level of compliance of the user by the compliance score generator 122 is accurate. Also, in some examples, the process for obtaining measurements is simpler for the user, eliminating user confusion, frustration, and/or error to help promote continued compliance with the medical care plan for the user. In some examples, the measurement devices 190A-N can be coded, for example by a serial number, so that the measurement devices 190A-N can be tracked. In some examples, the measurement devices 190A-N can be color coded to match the color of the instructions displayed on the user device 180A-N via the healthcare platform 110. The user can then easily determine which measurement device 190A-N is needed to correlate with the measurement solicited at that time. This can eliminate the need for the user to know and understand which measurement device 190A-N is needed, especially given various user's differing education and/or language levels. The user can then interact with the healthcare platform 110 and/or measurement device 190A-N to improve compliance with the medical care plan.

In at least one aspect, the platform 110 transmits the medical care plan to the user device 180A-N to encourage the user to follow the medical care plan (e.g., take medication, engage in physical activity, take a measurement via a measurement device 190A-N, etc.); gather data regarding the user, their health, and compliance with the medical care plan; and receives from the user device 180A-N data for further analyzing thereby improving compliance with the medical care plan and management of medical conditions.

Figure 2:
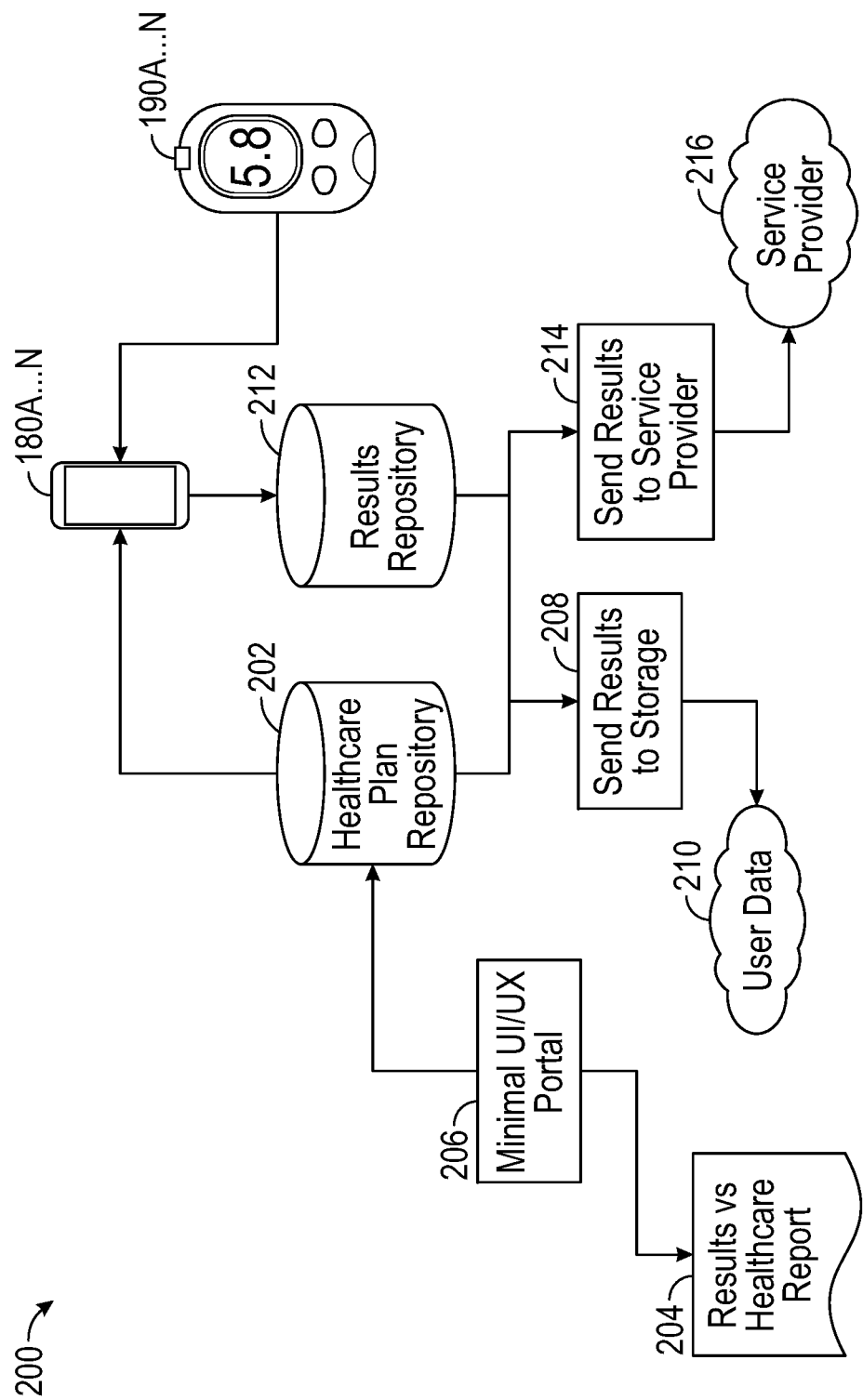
FIG. 2 illustrates an example process for utilizing the healthcare platform.

For example, referring to FIGS. 1 and 2, a customized medical care plan can be generated based on a health condition of the user. The customized medical care plan can include solicitations for a plurality of measurements, each measurement to be captured within a corresponding predetermined time period (e.g., before breakfast such as between 5:00 am-7:00 am, with breakfast such as between 7:00 am-8:30 am, before lunch such as 8:30 am-11:00 am, with lunch such as 11:00 am-1:00 pm, etc.). In some examples, the medical care plan can be generated via input from one or more service provider systems 195, such as from healthcare providers associated with a particular user. In some examples, the medical care plan can be generated by the healthcare platform 110 using, for example, the user data 160. For example, a healthcare provider, after seeing a patient, can determine what aspects of the patient's health need to be tracked and/or what medicines need to be taken. For example, if the patient has diabetes, the treatment can include glucose readings that need to be taken before and after each meal (e.g., breakfast, lunch, dinner). These requirements can be input into the healthcare platform 110 by the doctor and/or by the service provider via the service provider systems 195. In some examples, the information (e.g., diabetes) may be stored into the user data 160. The healthcare platform 110, for example via the medical care plan generator 120, can then take the input data regarding the health condition and treatment(s) to generate a customized medical care plan for the patient. The medical care plan can be provided to a user device 180A-N, for example via the healthcare platform 110. The medical care plan can be organized and displayed such that the user can easily identify what steps to take at what time, regardless of education and/or language level.

In some embodiments, the platform 110 may provide an interface (e.g., an API) that enables the user device 180A-N and measurement devices 190A-N, such as heart monitors, blood pressure monitors, scales, and/or other devices that may be used to collect information or data about a user, to receive a request for data from the platform 110, and to transmit data to the platform 110.

The data displayed to the user may be provided in different languages, such as English and Spanish. In some example aspects, one or more servers 115 of the platform 110 may provide application data and content for display on the user device 180A-N. The content can include a graphical user interface, such as the graphical user interface illustrated in FIGS. 4-10. The content can also include text or a web link. Of course, other types of content can also be provided. In some example aspects, the content can be transmitted from the one or more servers 115 via the network 105 to the user device 180A-N. In other example aspects, the content can be stored in a storage component (e.g., hard disk, RAM, ROM, etc.) of the respective user device 180A-N.

FIG. 2 illustrates an example process for utilizing the healthcare platform. The user device 180A-N is operable to receive a medical care plan via a healthcare plan repository 202. The healthcare plan repository 202 can receive the medical care plan and/or changes to the medical care plan via a minimal UI/UX portal 206. In at least one example, the UI/UX portal 206 can generate a results vs. healthcare report 204. In some examples, the healthcare plan repository 202 can send the medical care plan to storage 208 to be stored in user data 210. In some examples, the healthcare repository 202 can send the medical care plan, as shown in block 214, to the service provider 216. The user device 180A-N can receive one or more measurements from corresponding one or more measurement devices 190A-N. Each of the measurements from the measurement devices 190A-N correspond with a predetermined time period with which the measurement is to be taken as per the medical care plan. The user device 180A-N can transmit, in some examples via the results repository 212, the measurements to be stored in user data 210 via block 208 and/or to service provider 216 via block 214.

Upon receiving the measurement(s) from the corresponding measurement device(s) 190A-N within the corresponding predetermined time period(s), a compliance score can be generated. In some examples, the compliance score can be generated based on receipt or non-receipt of the remaining measurements of the plurality of measurements that are captured within the corresponding predetermined time periods. For example, the compliance score can be generated based on a percentage of receipt versus non-receipt of measurements within the predetermined time periods. In some examples, different measurements may be weighted based on importance.

Based on the generated compliance score and/or the one or more measurement(s) taken, an intervention can be initiated. For example, when the compliance score is outside of a predetermined threshold or predetermined range, the intervention may be initiated. For example, the user may have missed a number of measurements at the corresponding predetermined period(s) of time. Each missed measurement can lower the compliance score. The compliance score can be transmitted to the service provider 216 such that the service provider 216 can initiate the intervention when the compliance score is below a predetermined threshold. In some examples, the healthcare platform 110 can issue a notification to the service provider 216 when the compliance score is outside of the predetermined threshold or predetermined range. In some examples, the intervention can include an alert to the user or communicative contact with the user. Accordingly, the intervention improves compliance with the medical care plan since the service provider 216 can reach out and discuss and/or correct any issues that the user is experiencing.

In some examples, the measurement may be analyzed to determine whether the measurement is within a predetermined range of values. The intervention may be initiated when the measurement and/or a threshold number of measurements fall outside of the predetermined range of values. For example, the service provider 216, via service provider systems 195, can monitor the measurement(s) and/or compliance score and determine whether an intervention is to be initiated. The measurement can be transmitted to the service provider 216, and the service provider 216 can initiate the intervention. In some examples, the healthcare platform 110 can issue a notification to the service provider 216 when the measurement and/or threshold number of measurements is outside of the predetermined range of values. In some examples, the intervention can include an alert to the user or communicative contact with the user. Accordingly, the intervention improves compliance with the medical care plan since the service provider 216 can reach out and discuss and/or correct any issues that the user is experiencing.

Figure 3:
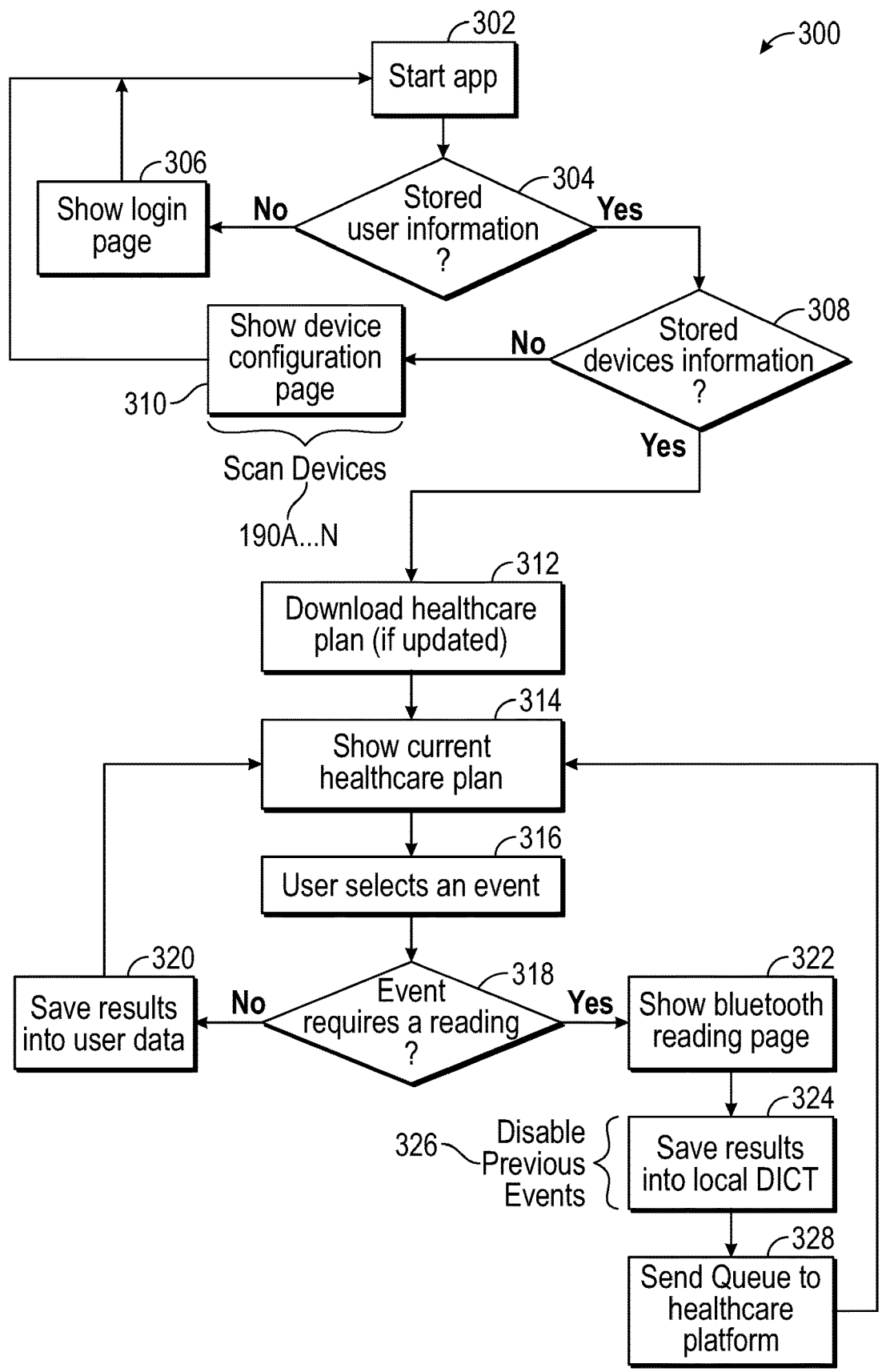
FIG. 3 illustrates an example flow chart for utilizing the healthcare platform.
Figure 4:
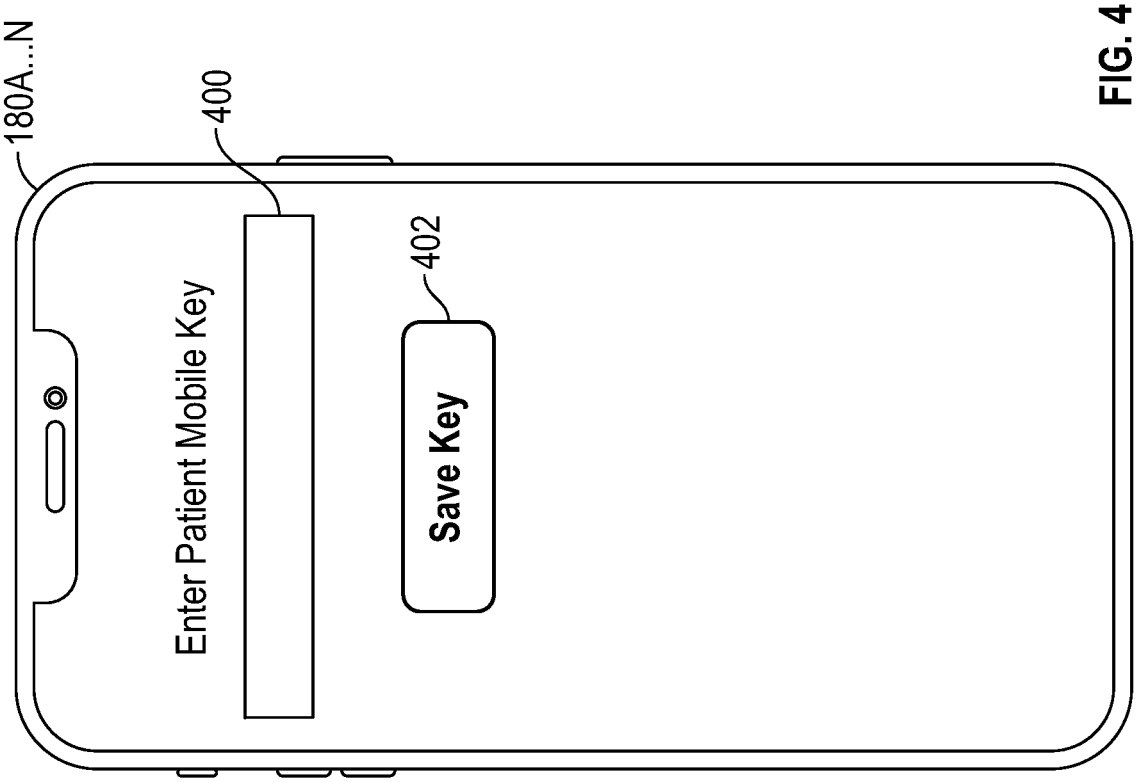
FIG. 4 illustrates an example graphical user interface of a healthcare platform.

FIG. 3 illustrates an example process 300 for utilizing a healthcare platform to treat a medical condition, in accordance with various aspects of the subject technology. Following start block 302, a user accesses the platform via a user device, for example via an app on the user device. The user may create an account and grant the platform access to the user's medical records, health data, wearable data, family history data, and/or medication data. The data may be stored in a database accessible by the platform for analyzing, generation of, and/or providing a customized medical care plan for medically treating a medical condition. For example, as shown in FIG. 4, a patient mobile key or unique identifier is required to access the platform. The user can input the key in input box 400 and press save key button 402 to access the platform.

Figure 5:
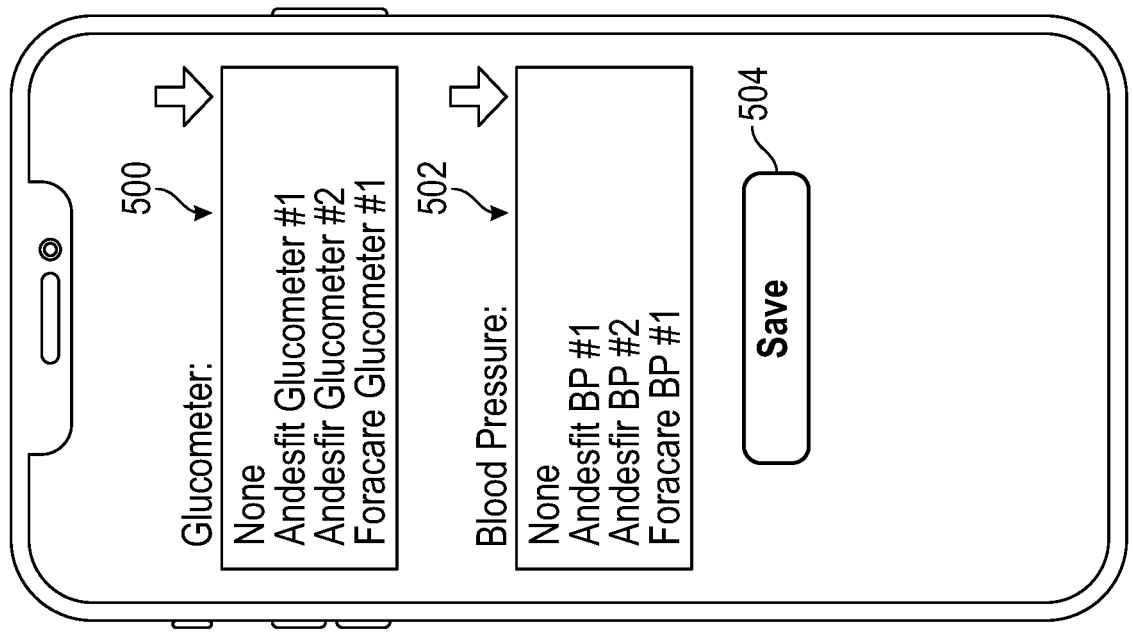
FIG. 5 illustrates an example graphical user interface of a healthcare platform.

At step 304, it can be determined if there is stored user information. If not, at step 306, the login page (e.g., as shown in FIG. 4) may be displayed. If yes, at block 308, it can be determined whether there is any stored devices information. For example, the user device can determine whether any measurement devices and/or the corresponding connections are stored and/or previously used. If not, at step 310, the device configuration page can be displayed, where the measurement devices 190A-N can be scanned and/or communicatively coupled with the user device. For example, as illustrated in FIG. 5, the glucometer selection box 500 allows a user to select the glucometer to be used and/or coupled with the user device. The blood pressure box 502 allows a user to select the blood pressure monitor to be used and/or coupled with the user device. Other measurement devices 190A-N can also be provided. When the selections are completed, the user can select the save button 504 to save the measurement devices 190A-N to be used and/or coupled with the user device.

A customized medical care plan can be generated based on a health condition of a user. The customized medical care plan can include solicitations for measurements, with each measurement to be captured within a corresponding predetermined time period. At step 312, the healthcare plan or customized medical care plan can be downloaded and provided to a user device. At step 314, the current medical care plan can be displayed via the user device to a user.

Figures 6, 7:
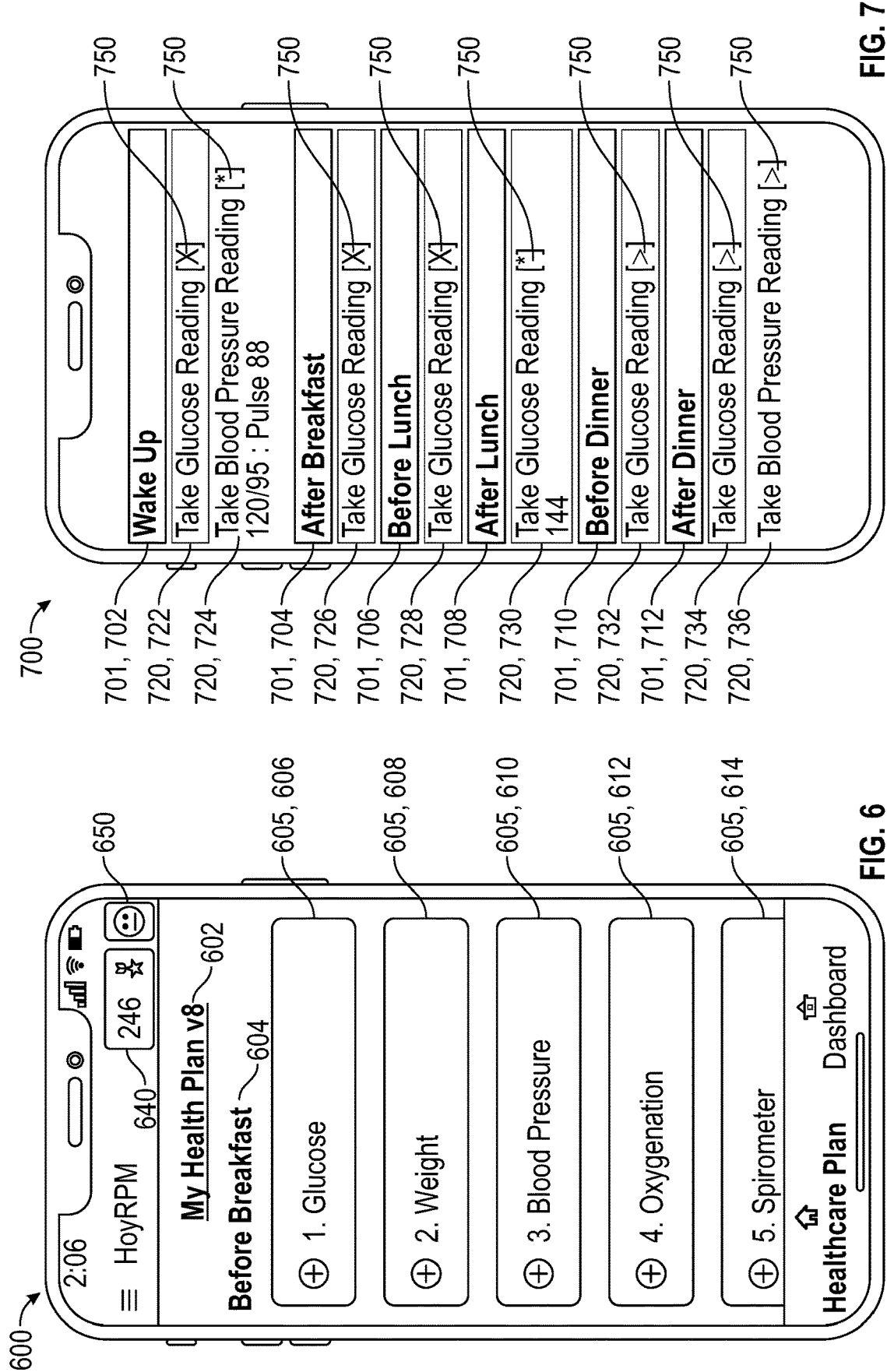
FIG. 6 illustrates an example graphical user interface of a healthcare platform.
FIG. 7 illustrates an example graphical user interface of a healthcare platform.

For example, FIGS. 6 and 7 illustrate examples of medical care plans being displayed on a user device. As illustrated in FIG. 6, the version of the medical care plan is shown in the title 602. By showing the version, the user is able to determine whether the most up to date medical care plan is being provided. Heading 604 can indicate the predetermined time period within which the measurements 605 are to be taken. For example, heading 604 shows "Before Breakfast." Accordingly, measurements 605 such as glucose 606, weight 608, blood pressure 610, oxygenation 612, and spirometer 614 are to be taken before breakfast. To determine whether the measurements 605 are taken before breakfast, a time period may be assigned to "Before Breakfast," such as 5:00 am to 7:00 am. The measurements 605 that correspond with the predetermined time period 604 are then to be taken between 5:00 am and 7:00 am. In some examples, the predetermined time period 604 may correlate with additional measurements of intake such as determining whether the user consumed food at a time which can correlate with breakfast (e.g., before 9:30 am).

As shown in FIG. 6, a compliance indicator 650 can be displayed. The compliance indicator 650 can be a simple icon, symbol, or any indicator to show the user how well they are complying with the medical care plan. For example, the compliance indicator 650 can correspond with the compliance score. As shown in FIG. 6, the compliance indicator 650 is displaying a moderate face. Accordingly, the compliance score is not too low but is not high, and the user can easily understand that they are not doing badly but can improve their compliance with the medical care plan.

Also as shown in FIG. 6, points 640 can be accumulated based on the user's compliance with the medical care plan. For example, the points 640 can correlate with the compliance score. The points 640 can be accumulated each time a measurement is received within the corresponding time period. In some examples, points 640 can be subtracted upon determination of non-receipt of a measurement within a corresponding time period. In some examples, the points 640 can lead to prizes and/or rewards, for example gift cards. This gamification can further promote compliance with the medical care plan.

As illustrated in FIG. 7, the predetermined time period 701 (e.g., Wake Up 702, After Breakfast 704, Before Lunch 706, After Lunch 708, Before Dinner 710, and After Dinner 712) to take the measurements 720 are also provided. For example, after Wake Up 702 and Before Breakfast 604, the medical care plan solicits glucose reading 722 and blood pressure reading 724. After Breakfast 704, the medical care plan solicits a glucose reading 726. Before Lunch 706, the medical care plan solicits a glucose reading 728. After Lunch 708, the medical care plan solicits a glucose reading 730. Before Dinner 710, the medical care plan solicits a glucose reading 732. After Dinner 712, the medical care plan solicits a glucose reading 734 and a blood pressure reading 736. By soliciting the measurements at easy to understand time periods, the user can more easily comply with the medical care plan.

As shown in FIG. 7, a badge 750 can be provided to indicate receipt of a measurement 720 within the corresponding predetermined time 701 (e.g., blood pressure reading 724, glucose reading 730), non-receipt of a measurement 720 within the corresponding predetermined time 701 (e.g., glucose reading 722, glucose reading 726, glucose reading 728), and/or to be taken in a future predetermined time 701 (e.g., glucose reading 732, glucose reading 734, blood pressure reading 736). The badge 750 can show the user how well the user has been complying with the medical care plan and promote improvement of compliance with the medical care plan.

Referring back to FIG. 3, at step 316, the user selects an event. In at least one example, a measurement is solicited at a corresponding predetermined time period according to the customized medical care plan. At step 318, it is determined whether the event requires a reading, for example receipt of a measurement from a measurement device. If not, at step 320, the results can be saved into user data (e.g., user data 210 in FIG. 2), and the process 300 continues to step 314 in displaying the current medical care plan.

Figure 8:
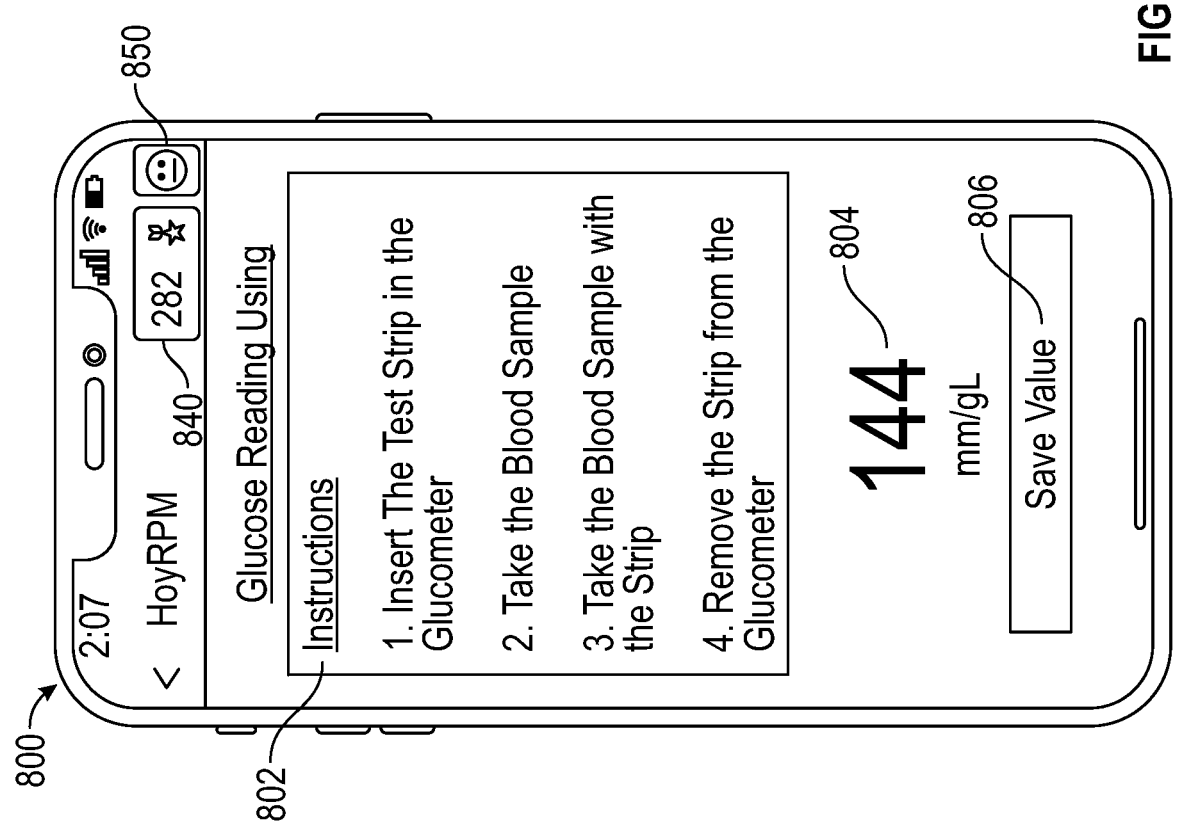
FIG. 8 illustrates an example graphical user interface of a healthcare platform.

If a reading is required, at block 322, the measurement device page can be shown. For example, as shown in FIG. 8, the measurement device page 800 includes a glucose reading interface. While FIG. 8 illustrates a glucose reading interface, other measurement device pages can be shown such as spirometer, blood pressure monitor, scale, etc. The measurement device page 800 can include instructions 802 on how to operate the measurement device and obtain a corresponding measurement. For example, as illustrated in FIG. 8, the instructions for the glucose reading interface include "1. Insert the Test Strip in the Glucometer. 2. Take the Blood Sample. 3. Take the Blood Sample with the Strip. 4. Remove the Strip from the Glucometer." The instructions are simple and easy to understand for users of differing education levels. Also, the instructions are shown in English in FIG. 8, but can be other languages depending on the user. Upon receipt of the measurement, the measurement 804 is displayed (e.g., 144 mm/gL). In some examples, as illustrated in FIG. 8, the user can save the measured value by pressing the "Save Value" button 806. In some examples, the measurement 804 is automatically saved upon receipt of the measurement from the measurement device. Accordingly, the user cannot manipulate the measurements or take multiple measurements until a desired measurement is obtained. Also, in some examples, similar to FIG. 6, a compliance indicator 850 and/or points 840 can be displayed.

Figure 9:
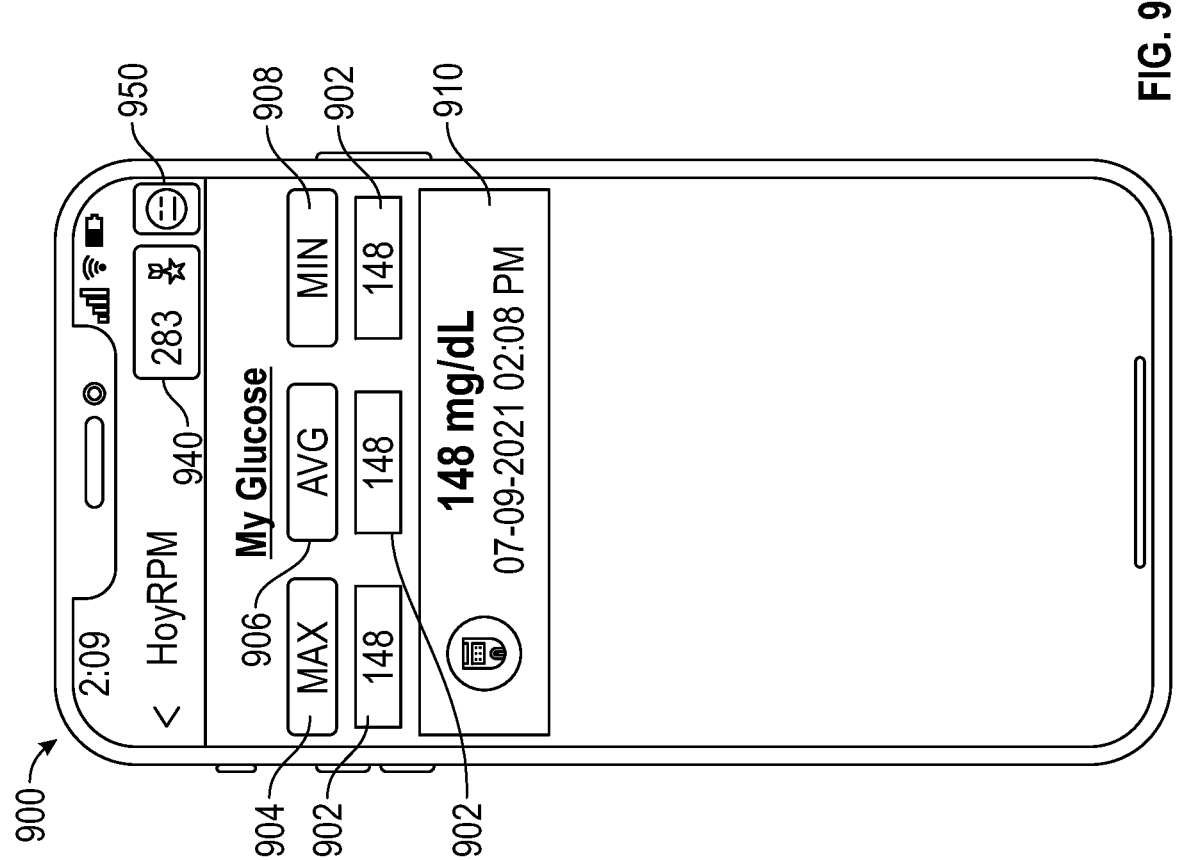
FIG. 9 illustrates an example graphical user interface of a healthcare platform.
Figure 10:
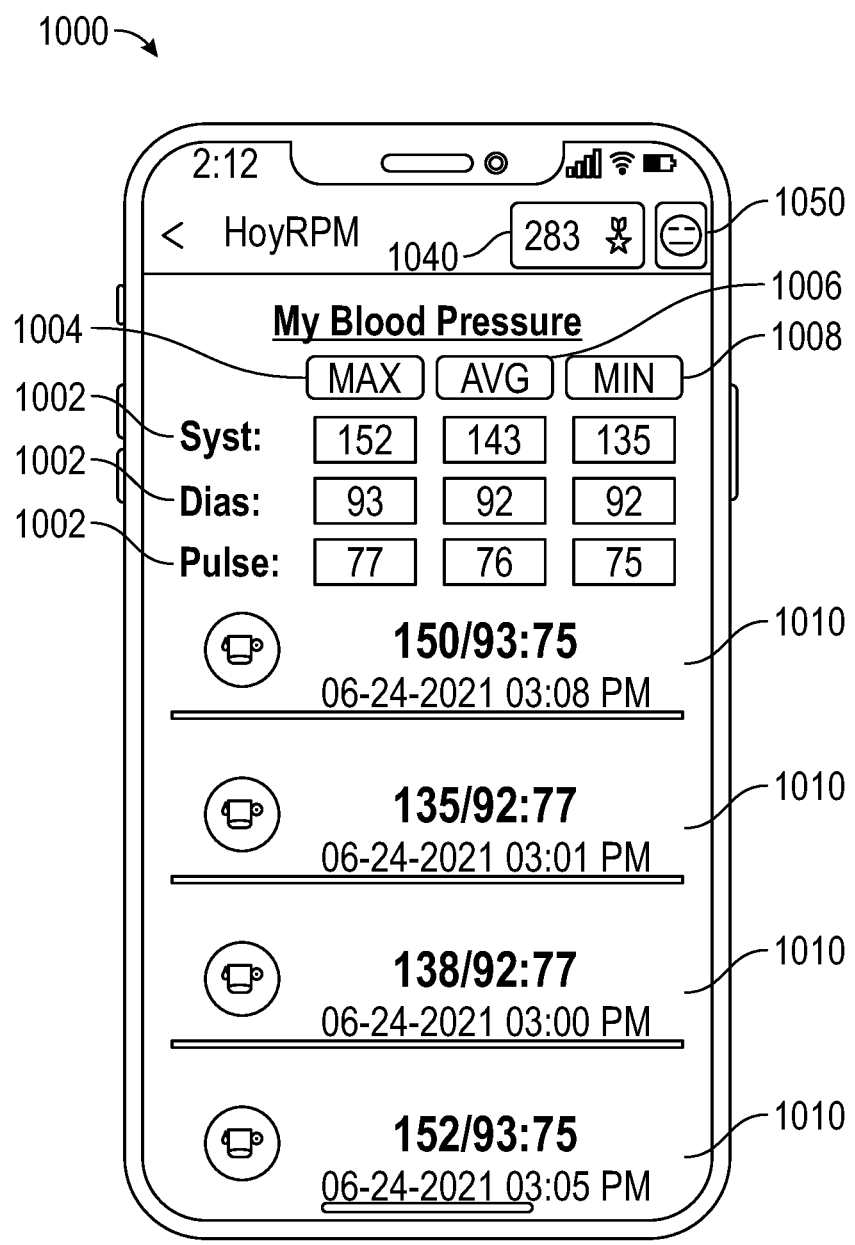
FIG. 10 illustrates an example graphical user interface of a healthcare platform.

At step 324, the results or measurements are saved, for example into a local dictionary network protocol. As shown in FIGS. 9 and 10, the measurements and/or analysis of the measurements can be saved and/or displayed. As shown in FIG. 9, the analysis of the measurements can include determining a maximum (e.g., highest) measurement 904, an average of the measurements 906, and/or a minimum (e.g., lowest) measurement 908. As shown in FIG. 9, only one measurement 910 has been taken, so the measurements 902 for the maximum 904, average 906, and minimum 908 are all 148 mg/dL. As shown in FIG. 9, the date and/or time that the measurement 910 was taken can also be recorded. Also, in some examples, similar to FIG. 6, a compliance indicator 950 and/or points 940 can be displayed.

As shown in FIG. 10, multiple measurements 1010 are taken. Additionally, the measurements 1010 include different measurements. For example, systolic blood pressure, diastolic blood pressure, and pulse are taken. As shown in FIG. 10, the analysis of the measurements can include determining a maximum (e.g., highest) measurement 1004, an average of the measurements 1006, and/or a minimum (e.g., lowest) measurement 1008. As shown in FIG. 10, the maximum 1004, average 1006, and minimum 1008 of the measurements 1002 for systolic blood pressure, diastolic blood pressure, and pulse are determined and/or displayed. As shown in FIG. 10, the date and/or time that the measurements 1010 were taken can also be recorded. Also, in some examples, similar to FIG. 6, a compliance indicator 1050 and/or points 1040 can be displayed.

At step 326, upon receipt of a measurement, user access to prior solicitations for the plurality of measurements can be disabled. Prior solicitations can include measurements corresponding with predetermined time periods that are prior to the predetermined time period corresponding to the selected and/or received measurement. For example, as illustrated in FIG. 7, when glucose reading 730 is taken After Lunch 708, all prior solicitations (e.g., glucose reading 722, blood pressure reading 724, glucose reading 726, glucose reading 728) are disabled. By disabling the prior solicitations, manipulation, cheating, and/or faking measurements are prevented, and the compliance score can accurately reflect the user's compliance. Accordingly, the service provider and/or doctor can confidently determine whether the user is complying with the medical care plan and/or can determine how to address any issues the user may be having in complying with the medical care plan.

At step 328, the queue can be sent to the healthcare platform. In some examples, the medical care plan can be revised based on receipt of the remaining measurements of the plurality of measurements. The medical care plan can be revised by the doctor, the service provider, and/or the healthcare platform.

If at any point in the process the compliance score and/or measurement(s) is outside of a predetermined threshold or predetermined range, an intervention can be initiated based on the generated compliance score and measurement(s). The intervention can include an alert to the user and/or communicative contact with the user, for example by the service provider.

Many of the above-described features and applications are implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 11:
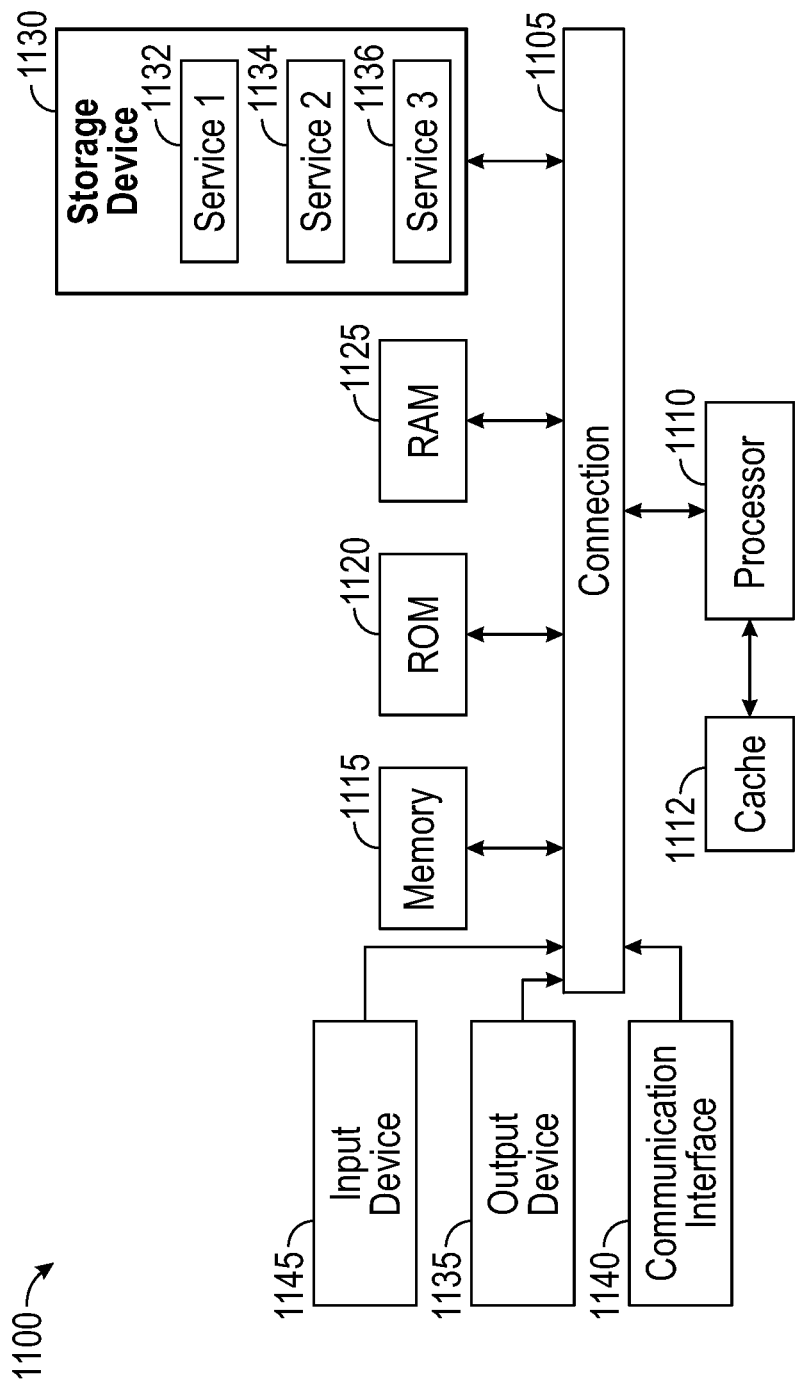
FIG. 11 illustrates an example of a system configured to treat a medical condition by improving compliance using an healthcare platform, in accordance with some aspects.

FIG. 11 illustrates an example of a system 1100 configured to treat a medical condition with a customized medical care plan, in accordance with some aspects. A platform which some implementations of the subject technology are implemented may include various types of computer readable media and interfaces for various other types of computer readable media. One or more components of the platform are in communication with each other using connection 1105. Connection 1105 can be a physical connection via a bus, or a direct connection into processor 1110, such as in a chipset architecture. Connection 1105 can also be a virtual connection, networked connection, or logical connection.

In some embodiments system 1100 is a distributed system in which the functions described in this disclosure can be distributed within a datacenter, multiple datacenters, a peer network, etc. In some embodiments, one or more of the described system components represents many such components each performing some or all of the function for which the component is described. In some embodiments, the components can be physical or virtual devices.

System 1100 includes at least one processing unit (CPU or processor) 1110 and connection 1105 that couples various system components including system memory 1115, such as read only memory (ROM) 1120 and random access memory (RAM) 1125 to processor 1110. Computing system 1100 can include a cache 1112 of high-speed memory connected directly with, in close proximity to, or integrated as part of processor 1110.

Processor 1110 can include any general purpose processor and a hardware service or software service, such as services 1132, 1134, and 1136 stored in storage device 1130, configured to control processor 1110 as well as a special-purpose processor where software instructions are incorporated into the actual processor design. The instructions may generate a medical care plan, compliance score, and/or cause an intervention, as described above. Processor 1110 may essentially be a completely self-contained computing system, containing multiple cores or processors, a bus, memory controller, cache, etc. A multi-core processor may be symmetric or asymmetric.

To enable user interaction, computing system 1100 includes an input device 1145, which can represent any number of input mechanisms, such as a microphone for speech, a touch-sensitive screen for gesture or graphical input, keyboard, mouse, motion input, speech, etc. Computing system 1100 can also include output device 1135, which can be one or more of a number of output mechanisms known to those of skill in the art, and may include, for example, printers and display devices, such as cathode ray tubes (CRT) or liquid crystal displays (LCD). Some implementations include devices such as a touch screen that functions as both input and output devices. In some instances, multimodal systems can enable a user to provide multiple types of input/output to communicate with computing system 1100. Computing system 1100 can include communications interface 1140, which can generally govern and manage the user input and system output. There is no restriction on operating on any particular hardware arrangement and therefore the basic features here may easily be substituted for improved hardware or firmware arrangements as they are developed.

Storage device 1130 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read only memory (ROM), and/or some combination of these devices.

The storage device 1130 can include software services, servers, services, etc., that when the code that defines such software is executed by the processor 1110, it causes the system to perform a function. In some embodiments, a hardware service that performs a particular function can include the software component stored in a computer-readable medium in connection with the necessary hardware components, such as processor 1110, connection 1105, output device 1135, etc., to carry out the function.

It will be appreciated that computing system 1100 can have more than one processor 1110, or be part of a group or cluster of computing devices networked together to provide greater processing capability.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

It is understood that any specific order or hierarchy of steps in the processes disclosed is an illustration of exemplary approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more.

All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A method for improving compliance with a customized medical care plan, the method comprising:
   generating a customized medical care plan based on a health condition of a user, the customized medical care plan including solicitations for a plurality of measurements, each measurement to be captured within a corresponding predetermined time period;
   soliciting a first measurement of the plurality of measurements at a first predetermined time period according to the customized medical care plan;
   receiving, by a computing device from a measurement device and over a network, the first measurement within the first predetermined time period, the first measurement comprising one or more at least one of a glucose reading, an oxygen reading, a ventilation reading, a blood pressure measurement, a heart rate, or a weight associated with the user, wherein the measurement device is configured to prevent the user from retaking the first measurement using the measurement device prior to sending the first measurement to the computing device;
   disabling a user access to one or more prior solicitations for one or more measurements to be captured within one or more predetermined time periods, wherein the disabling of the user access to the one or more prior solicitations is automatically triggered by the receiving of the first measurement from the measurement device;
   generating, by the computing device, a compliance score based on receipt of the first measurement within the first predetermined time period; and
   initiating an intervention based on the generated compliance score and the first measurement.

2. The method of claim 1, further comprising determining whether the first measurement is within a predetermined range of values, wherein the intervention is initiated when the first measurement falls outside of the predetermined range of values.

3. The method of claim 1, further comprising:
   increasing the compliance score each time a measurement of the plurality of measurements is received within a respective predetermined time period and decreasing the compliance score each time a measurement of the plurality of measurements is not received within a respective predetermined time period.

4. The method of claim 1, further comprising communicatively coupling the measurement device associated with the first measurement with the user device.

5. The method of claim 1, further comprising transmitting the first measurement to a service provider, wherein the service provider initiates the intervention.

6. The method of claim 5, further comprising issuing a notification to the service provider when the first measurement is outside of a predetermined range of values.

7. The method of claim 1, further comprising causing to be displayed a compliance indicator that corresponds with the generated compliance score.

8. The method of claim 1, wherein the compliance score is generated based on receipt or non-receipt of measurements of the plurality of measurements that are captured within the corresponding predetermined time periods.

9. The method of claim 7, further comprising revising the customized medical care plan based on receipt of the measurements of the plurality of measurements.

10. The method of claim 1, wherein the intervention comprises an alert to the user or communicative contact with the user.

11. A medical care compliance system comprising:
one or more processors; and
a non-transitory computer-readable medium storing instructions that, when executed by the processors, cause the processors to perform operations comprising:
generating a customized medical care plan based on a health condition of a user, the customized medical care plan including solicitations for a plurality of measurements, each measurement to be captured within a corresponding predetermined time period;
soliciting a first measurement of the plurality of measurements within a first predetermined time period according to the customized medical care plan;
receiving, from a measurement device and over a network, the first measurement within the first predetermined time period, the first measurement comprising one or more at least one of a glucose reading, an oxygen reading, a ventilation reading, a blood pressure measurement, a heart rate, or a weight associated with the user, wherein the measurement device is configured to prevent the user from retaking the first measurement using the measurement device prior to sending the first measurement to the computing device;
disabling a user access to one or more prior solicitations for one or more measurements to be captured within one or more predetermined time periods, wherein the disabling of the user access to the one or more prior solicitations is automatically triggered by the receiving of the first measurement from the measurement device;
generating a compliance score based on receipt of the first measurement within the first predetermined time period; and
initiating an intervention based on the generated compliance score and the first measurement.

12. The system of claim 11, wherein the processors are further configured to perform operations comprising transmitting the first measurement to a service provider.

13. The system of claim 11, wherein the processors are further configured to perform operations comprising causing to be displayed a compliance indicator that corresponds with the generated compliance score.

14. The system of claim 11, wherein the compliance score is generated based on receipt or non-receipt of measurements of the plurality of measurements that are captured within the corresponding predetermined time periods.

15. The system of claim 11, wherein the processors are further configured to perform operations comprising increasing the compliance score each time a measurement of the plurality of measurements is received within a respective predetermined time period and decreasing the compliance score each time a measurement of the plurality of measurements is not received within a respective predetermined time period.

16. The system of claim 11, wherein the first measurement device comprises at least one of a glucometer, a scale, a blood pressure monitor, an oxygenation monitor, and/or a spirometer.

17. The system of claim 11, wherein the intervention comprises an alert to the user or communicative contact with the user.

18. A non-transitory computer-readable medium comprising instructions, the instructions, when executed by one or more processors, cause the processors to perform operations comprising:
generating a customized medical care plan based on a health condition of a user, the customized medical care plan including solicitations for a plurality of measurements, each measurement to be captured within a corresponding predetermined time period;
soliciting a first measurement of the plurality of measurements within a first predetermined time period according to the customized medical care plan;
receiving, from a measurement device and over a network, the first measurement within the first predetermined time period, the first measurement comprising one or more at least one of a glucose reading, an oxygen reading, a ventilation reading, a blood pressure measurement, a heart rate, or a weight associated with the user, wherein the measurement device is configured to prevent the user from retaking the first measurement using the measurement device prior to sending the first measurement to the computing device;
disabling a user access to one or more prior solicitations for one or more measurements to be captured within one or more predetermined time periods, wherein the disabling of the user access to the one or more prior solicitations is automatically triggered by the receiving of the first measurement from the measurement device;
generating a compliance score based on receipt of the first measurement within the first predetermined time period; and
initiating an intervention based on the generated compliance score and the first measurement.

19. The non-transitory computer-readable medium of claim 18, wherein the instructions are further configured to cause the processors to perform operations comprising increasing the compliance score each time a measurement of the plurality of measurements is received within a respective predetermined time period and decreasing the compliance score each time a measurement of the plurality of measurements is not received within a respective predetermined time period.

20. The non-transitory computer-readable medium of claim 18, wherein the compliance score is generated based on receipt of measurements of the plurality of measurements captured within the corresponding predetermined time periods; and wherein the instructions are further configured to cause the processors to revise the customized medical care plan based on receipt of the measurements of the plurality of measurements.

* * * * *